US00PP12507P2

(12) United States Plant Patent
Slaughter et al.

(10) Patent No.: US PP12,507 P2
(45) Date of Patent: Apr. 2, 2002

(54) PEACH TREE NAMED 'BURPEACHTHREE'

(75) Inventors: John K. Slaughter, Clovis; Timothy J. Gerdts, Kingsburg, both of CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 09/455,973

(22) Filed: Dec. 6, 1999

(51) Int. Cl.[7] ..... A01H 5/00
(52) U.S. Cl. ..... Plt./197

(58) Field of Search ..... Plt./197

*Primary Examiner*—Bruce R. Campell
*Assistant Examiner*—Susan B. McCormick
(74) *Attorney, Agent, or Firm*—Wells, St. John, Roberts, Gregory & Matkin, P.S.

(57) ABSTRACT

A new and distinct variety of peach tree denominated varietally as 'Burpeachthree', and which is characterized as to novelty by producing an attractively colored fruit which is ripe for commercial harvesting and shipment approximately August 30 to September 5 under the ecological conditions prevailing in the San Joaquin Valley of Central California.

1 Drawing Sheet

BACKGROUND OF THE NEW VARIETY

The present invention relates to a new, novel and distinct variety of peach tree, which has the denominated varietally as 'Burpeachthree'. The 'Burpeachthree' Peach produces an exceptionally high quality, clingstone peach which matures in the late season. Another unique aspect of the 'Burpeachthree' is that it yields a firm peach that exhibits very high eating quality as compared with other peach tree varieties which mature at approximately the same time.

ORIGIN

The present peach tree variety was the result of an ongoing program of fruit and nut tree breeding. The purpose of this program is to improve the commercial quality of deciduous fruit and nut varieties and rootstocks by creating and releasing promising selections of prunus, malus and regia species. To this end, we make both controlled and hybrid crosses each year in order to produce seedling populations from which improved progenies are evaluated and selected.

The seedling 'Burpeachthree' was originated by the inventors in 1993, and chosen from among a population of seedlings which were initially derived from a controlled cross of the peach tree 'Autumn Lady', (U.S. Plant Pat. No. 4,398), which was used as the seed parent, and the 'Summer Lady' peach tree (U.S. Plant Pat. No. 5,865), which was used as the seed pollen parent. The resulting seed from this controlled cross were planted in the spring of 1994. The new variety was selected from among the seedlings growing in the experimental orchards of the Assignee, which is located near the city of Fowler, Calif., County of Fresno, in the central portion of the San Joaquin Valley of Calif. The 'Burpeachthree' was marked for subsequent observation and noted as having exceptional characteristics. It was subsequently evaluated during the 1995–1999 fruiting seasons. After the 1995 season, 'Burpeachthree' was selected for advanced evaluation and repropagation.

ASEXUAL REPRODUCTION

Scionwood from the original seedling of the peach tree 'Burpeachthree' was subsequently grafted onto two different and existing 'Nemared' (non-patented) peach rootstocks in 1996 in the evaluation plot on The Burchell Nursery's experimental farm previously described. Fruit from the resulting propagation has been evaluated for the 1997–2000 fruiting seasons. The age at observation was between 2 and 4 years. This evaluation clearly demonstrated that the repropagated trees are true to the characteristics of the original seedling in all observable aspects.

SUMMARY OF THE VARIETY

The 'Burpeachthree' peach tree is characterized as to novelty by producing fruit which ripens in late season; is very high in quality; very firm; and has an attractive exterior coloration. In this regard, the present variety of peach tree bears clingstone fruit which are ripe for commercial harvesting and shipment approximately August 30 to September 5. This is approximately the same harvest date as the common commercial freestone peach variety 'Fairtime'. Further, the present variety distinguishes itself from the 'Fairtime' Peach Tree by producing fruit which have a high exterior coloration, exceptional firmmess, a clingstone trait and extremely flavorful flesh quality.

BRIEF DESCRIPTION OF THE DRAWING

The accompanying drawing is a color photograph of a characteristic twig bearing typical leaves; several leaves showing both the dorsal and ventral coloration thereof, and several mature fruit showing their external coloration sufficiently matured for harvesting and shipment. Additionally, one fruit of the subject variety is dissected in the equatorial or cheek plane to illustrate the flesh and stone characteristics thereof.

DETAILED DESCRIPTION

Referring more specifically to the pomological details of this new and distinct variety of peach tree, the following has been observed under the ecological conditions prevailing near the town of Fowler, county of Fresno, state of Calif. All major color code designations are by reference to The R.H.S. Colour Chart (1995 Third Edition) provided by The Royal Horticultural Society of Great Britain.

Tree:

*Size*.—Generally — Average to above average as compared to other commom peach cultivars.

*Productivity*.—Productive. Productivity with respect to pounds per acre is not available.

*Figure*.—The original seedling was trained in a central leader configuration with a moderate spread in the crown of the tree. The tree is considered upright to upright spreading in form.

*Height*.—The original seedling had a height dimension of 3.8 m at the end of the 1999 growing season.

*Width*.—The original seedling tree had achieved a width of 2.16 m at the end of the 1999 growing season.

*Current season growth*.—The current season growth for the new variety was approximately 0.91–1.13 m.

*Regularity of bearing*.—Regular, and considered hardy under typical central San Joaquin Valley climatic conditions.

Trunk:

*Diameter*.—Approximately 95 mm in diameter when measured at a distance of approximately 15.24 cm above the soil level, at the end of the 1998 growing season.

*Bark texture*.—Considered moderately rough with numerous folds of papery scarf skin being present.

*Lenticels*.—Numerous flat, oval lenticels are present. The lenticels range in size from approximately 3.0 to 7.1 millimeters in width, and from approximately 1 to 2 millimeters in height.

*Lenticels*.—Color — Approximately RHS Greyed Orange Group 164 D.

*Bark coloration*.—Variable, but it is generally considered to be a grey-brown (RHS Greyed-Orange Group 174 B).

Branches:

*Size*.—Considered medium for the variety.

*Diameter*.—The branches have a diameter of 57 mm when measured during the 3$^{rd}$ year after grafting.

*Surface texture*.—Average, and appearing furrowed on wood which is several years old.

*Crotch angles*.—Variable between about 43° to 54° from the horizontal axis for scaffold limbs. This is not distinctive of the variety, however.

*Current season shoots*.—Surface texture — Substantially glabrous.

*Internode length*.—Approximately 2.3 to 2.5 cm.

*Color of mature branches*.—Medium brown, (RHS Greyed Orange Group 166 C to 200 C).

*Current season shoots*.—Color — Light green, (RHS Yellow Green Group 145 B), with some reddish-brown coloration appearing on exposed the exterior shoots (RHS Greyed Red Group 181 B). The color of the new shoot tips is considered a bright and shiny green (RHS Green Group 143 B).

Leaves:

*Size*.—Considered relatively large for the species. Leaf measurements have been taken from vigorous upright current season growth approximately at mid-shoot.

*Leaf length*.—Approximately 180 to 190 millimeters.

*Length width*.—Approximately 53 to 56 millimeters.

*Leaf thickness*.—Approximately 1 to 2 millimeters.

*Leaf base shape*.—The leaf base is slightly oblique.

*Leaf form*.—Lancelolate.

*Leaf tip form*.—Acuminate. The tip often appears flexed downwards and twisted laterally.

*Leaf color*.—Dark green, (RHS Green Group 137 A).

*Leaf texture*.—Substantially glabrous.

*Lower surface*.—Light green, (RHS Yellow Green Group 146 B).

*Venation*.—Pinnately net veined.

*Mid-vein*.—Color — Light yellow green, (RHS Yellow Green Group 150 D).

*Leaf margins*.—Form — Considered crenate, occasionally doubly crenate. Uniformity — Considered generally uniform.

*Leaf petioles*.—Size — Considered medium. Length — Approximately 6 to 10 millimeters. Diameter — Approximately 1.5 to 2 millimeters. Color — Pale green, (RHS Yellow Green Group 145 D).

*Leaf glands*.—Size — Approximately one to two millimeters in height and two to three millimeters in width. Numbers — Generally 2–3 per side, occasionally one per side. Type — Reniform. Color — Greenish brown (RHS Grey Brown 199 C).

*Leaf stipules*.—Size — Medium for the variety. Number — Typically (2) stipules per leaf bud and up to (6) per shoot. Length — Approximately 6 to 10 millimeters. Form — Linear in form with a serrated margin. Color — Green (RHS Green Group 135 B) when young but graduating to yellow-brown (RHS Greyed Orange Group 177 A) with advancing senescence. The stipules are considered to be early deciduous.

Flowers:

*Flower buds*.—Generally — The floral buds are considered to be medium in size (22–26 mm long), conic in form (16–19 mm wide), and slightly appressed relative to the bearing shoot.

*Flower buds*.—Color — The bud scales are gray-brown, (approximately RHS Greyed Orange Group 177 C). The buds are considered hardy under typical central San Joaquin Valley climatic conditions.

*Blooming type*.—Considered average in relation to other peach cultivars commonly growing in the central San Joaquin Valley. Date of full bloom was Mar. 4, 1998.

*Flower type*.—The variety is considered to be a showy type flower.

*Flower size*.—Flower diameter at full bloom is approximately 41 to 49 millimeters.

*Bloom quantity*.—Considered abundant.

*Flower bud frequency*.—Normally 1 to 2 buds appear per node, although 2 buds per node are more common than one.

*Petal size*.—Generally — Considered medium for the species. Length — Approximately 18 to 20 millimeters. Width — Approximately 16 to 19 millimeters.

*Petal form*.—Broadly ovate.

*Petal count*.—Nearly always 5.

*Petal color*.—Light pink when young, (approximately RHS Red Purple Group 68 C), and darkening with advancing senescence to a medium pink (RHS Red Purple Group 68 B). The lower portion of the flower is RHS Red Purple Group 68 A.

*Fragrance*.—None to occasionally slight.

*Petal claw*.—Form — The claw is considered truncate in shape and has a medium size when compared to other similar varieties. Length — Approximately 1.5 to 2.1 millimeters. Width — Approximately 1 millimeter.

*Petal margins*.—Generally considered variable, from nearly smooth, to highly undulate and ruffled, especially apically.

*Petal apex.*—Generally — The petal apices appear slightly domed.

*Flower pedicel.*—Length — Considered medium-short, and having an average length of approximately 2.0 to 2.8 millimeters. Diameter — Considered average, approximately 2 millimeters. Color — Bright green (RHS Yellow Green Group 144 D).

*Floral nectaries.*—Color — Dull orange to orange-gold (approximately RHS Greyed-Orange Group 169 D). The color of the nectaries become increasingly dull and slightly darker with advancing senescence.

*Calyx.*—Surface Texture — Generally glabrous. Color — A dull red, (approximately RHS Greyed Red Group 181 AB).

*Sepals.*—Surface Texture — The surface is covered with grey colored pubescence (RHS Greyed Green Group 198 D). Number — Generally (5) per flower. Size — Typically 4–5 mm wide and 5–6 mm in length, and ovate in form. Color — A dull red (approximately RHS Greyed Purple Group 184 B).

*Anthers.*—Generally — Average in size. Approximately 1.0 mm in width; and 1.0–1.5 mm in length. Color — Red to reddish-orange dorsally, (approximately RHS Greyed Red Group 178 C). Pollen Production — Pollen is abundant, and has a yellow-gold color, (approximately RHS Yellow Orange 19 A).

*Filaments.*—Size — Variable in length, approximately 14 to 16 millimeters. Color — White, (RHS Red Purple Group 69 D). and darkening with advanced maturity.

*Pistil.*—Generally — Average in size. Length — Approximately 15 to 17 millimeters, including the ovary. Color — Considered a very pale green when young, (approximately RHS Yellow Green Group 150 D), and becoming slightly more yellowish with advancing senescence.

*Surface texture.*—Pubescent.

Fruit:

*Maturity when described.*—The present variety of fruit is described, as it would be found in its firm ripe condition at full commercial maturity. In this regard, the fruit of the present variety was first picked on Aug. 30, 1998. The date of last pick of the same fruit in 1998 was approximately September 8 under the ecological conditions prevailing in the San Joaquin Valley of Central Calif.

*Size.*—Generally — Large and considered uniform.

*Average cheek diameter.*—Approximately 73 to 75 millimeters.

*Average suture diameter.*—Approximately 70 to 72 millimeters.

*Average axial diameter.*—Approximately 75 to 78 millimeters.

*Typical weight.*—178 grams. This is highly dependent upon cultural practices, and therefore is not distinctive of the present variety.

*Fruit form.*—Generally — Oblate in its lateral aspect. The fruit is generally uniform in symmetry with a slightly oval form when viewed from the apical aspect.

*Fruit suture.*—Generally — The suture appears as a thin line, which extends from the base to the apex, and appears slightly deeper, basally, within the stem well, and apically on both sides of the pistil point. No apparent callousing or stitching exists along the suture line.

*Suture.*—Color — The suture normally is the same color as the underlying blush, both the orange-yellow background, (RHS Yellow Group 13 D) and the red orange color (RHS Red Group 46 A) occur.

*Ventral surface.*—Form — Considered uniform.

*Stem cavity.*—Size — Considered moderately shallow for the species. Width — Approximately 8–11 millimeters.

*Length.*—Approximately 21–26 millimeters. Depth — Approximately 6 to 9 millimeters. Form — Considered narrowly oval. Fruit base — Generally — Considered truncate in form, and uniform. Fruit Apex — Generally — Considered depressed and usually recessed below the height of the apical shoulders.

*Fruit stem.*—Generally — Considered medium in length, approximately 7 to 11 millimeters. Diameter — Approximately 3 to 4 millimeters. Color — Generally a pale yellow-green (approximately RHS Yellow Green Group 145 B).

*Fruit skin.*—Generally — Considered medium or average in thickness. Surface Texture — The variety has very light, short pubescence. Skin Acidity — Considered neutral.

*Tenacious to flesh.*—Yes at commercial maturity.

*Tendency to crack.*—Not observed.

*Skin color.*—Generally — Variable, with approximately 60% to 80% of the fruit surface covered with an attractive red blush.

*Blush color.*—The blush color is generally more prevalent apically. This red blush color ranges from a dark red, (RHS Red Group 46 A) to red group, (RHS 47 C), with many degrees of shading and blending between these colorations.

*Skin ground color.*—This is generally present in variable percentages covering approximately 10% to 30% of the fruit's surface, and which is a yellow-golden color and which ranges from (RHS Yellow Orange Group 20 D to 22 A and includes the various hues between 20 D and 22 A).

*Flesh color.*—Generally — Considered variable from a yellow/orange, (RHS Yellow Orange Group 16 A to 16 D) to reddish orange, (approximately RHS Red Orange Group 45 B). This color can radiate into the flesh generally beginning at the exterior margin.

*Flesh fibers.*—Generally — Present, numerous in number, and light colored. These fibers are present throughout the flesh.

*Stone cavity.*—Color — Red, (approximately RHS Red Orange Group 45 B), to a yellow orange, (approximately RHS Yellow Orange Group 18 B). With increasing maturity, occasional red flecks can appear randomly in the flesh. These flecks are more numerous nearer the pit cavity than at the exterior margin.

*Flesh texture.*—Generally — The flesh is considered firm and fine at full commercial maturity.

*Ripening.*—Generally — The fruit of the present variety ripens evenly.

*Flavor.*—Considered very sweet and having mild acidity. The flavor is considered both pleasant and balanced.

*Aroma.*—Pleasant and abundant.

*Eating quality.*—Generally — Considered very good to excellent and well above average when compared to other common peach tree varieties.

Stone:

*Attachment*.—Gererally — The stone is considered a true clingstone at full commercial maturity.

*Stone size*.—Generally — Considered medium to medium-small.

*Length*.—Approximately 35 to 38 millimeters.

*Width*.—Approximately 26 to 32 millimeters.

*Diameter*.—Approximately 19 to 25 millimeters.

*Fibers*.—Generally — A few medium length fibers are attached along the entire surface of the stone.

*Stone form*.—Generally — The stone is considered oval.

*Stone base*.—The stone base is somewhat oblique.

*Base angle*.—The base angle of the stone is variable, but, most freguently is considered slightly oblique to the stone axis.

*Hilum*.—Generally — Considered medium in size, and relatively well defined. The hilum is approximately 5 to 6 millimeters long and approximately 3 to 4 millimeters wide. Form — Considered oval.

*Apex*.—Shape — The stone apex is raised and has an acute tip.

*Stone shape*.—Considered variable. The stone is normally unequal, although occasionally it may appear nearly equal.

*Stone surface*.—Surface Texture — Generally considered medium in roughness and exhibits substantial pitting laterally. Substantial grooving is apparent over the apical shoulders. Surface pitting is prominent generally, and is more frequently present basally. Ridges — Numerous fine ridges are present basally, and converge towards the base of the stone.

*Ventral edge*.—Width — Considered medium, and having a width dimension of approximately 4.5 to 6 millimeters at mid-suture with the wings. being most prominent over the basal area.

*Dorsal edge*.—Shape — Full, heavily grooved and having jagged edges. The dorsal edge is moderately eroded over the apical shoulder.

*Stone color*.—The color of the dry stone is a light to medium brown, (RHS Orange Red Group 31 C).

*Tendency to split*.—No splitting noted.

*Kernel*.—Gelatinous and immature when fruit is ripe. Form — Oval when the fruit is ripe. Length — Approximately 20–22 mm. Width — 16–19 mm. Thickness — 4–6 mm. Color — Approximately RHS Greyed-Orange Group 173 B. Pellicle — Slight pubescence.

*Use*.—The subject variety Peach tree Burpeachthree is considered to be a late maturing peach tree which produces a very firm, and attractively colored fruit for use in both local and long distance shipping and for the fresh market.

*Keeping quality*.—Fruit has stored will at 2° C. for 18 days.

*Resistance to insects and disease*.—No particular susceptibilities were noted.

*Hardiness*.—No winter injury has been noted during the several years of evaluation in the Central San Joaquin Valley. The current variety has not been intentionally subjected to drought or heat stress and therefore this information is not available.

*Shipping quality*.—Well above average.

Although the new variety of peach tree possesses the described characteristics as a result of the growing conditions prevailing in Fresno County, Calif., in the central part of the San Joaquin Valley, it is to be understood that variations of the usual magnitude and characteristics incident to growing conditions, fertilization, pruning, and pest control are to be expected.

Having thus described and illustrated our new Peach tree variety, what we claim is new and desire to secure by Plant Letters Patent is:

1. A new and distinct variety of peach tree substantially as shown and described and which is characterized principally as novelty by producing an attractively colored clingstone peach which is mature for havesting and shipment approximately August 30–September 5 under the ecological conditions prevailing in the San Joaquin Valley of Central Calif.

* * * * *

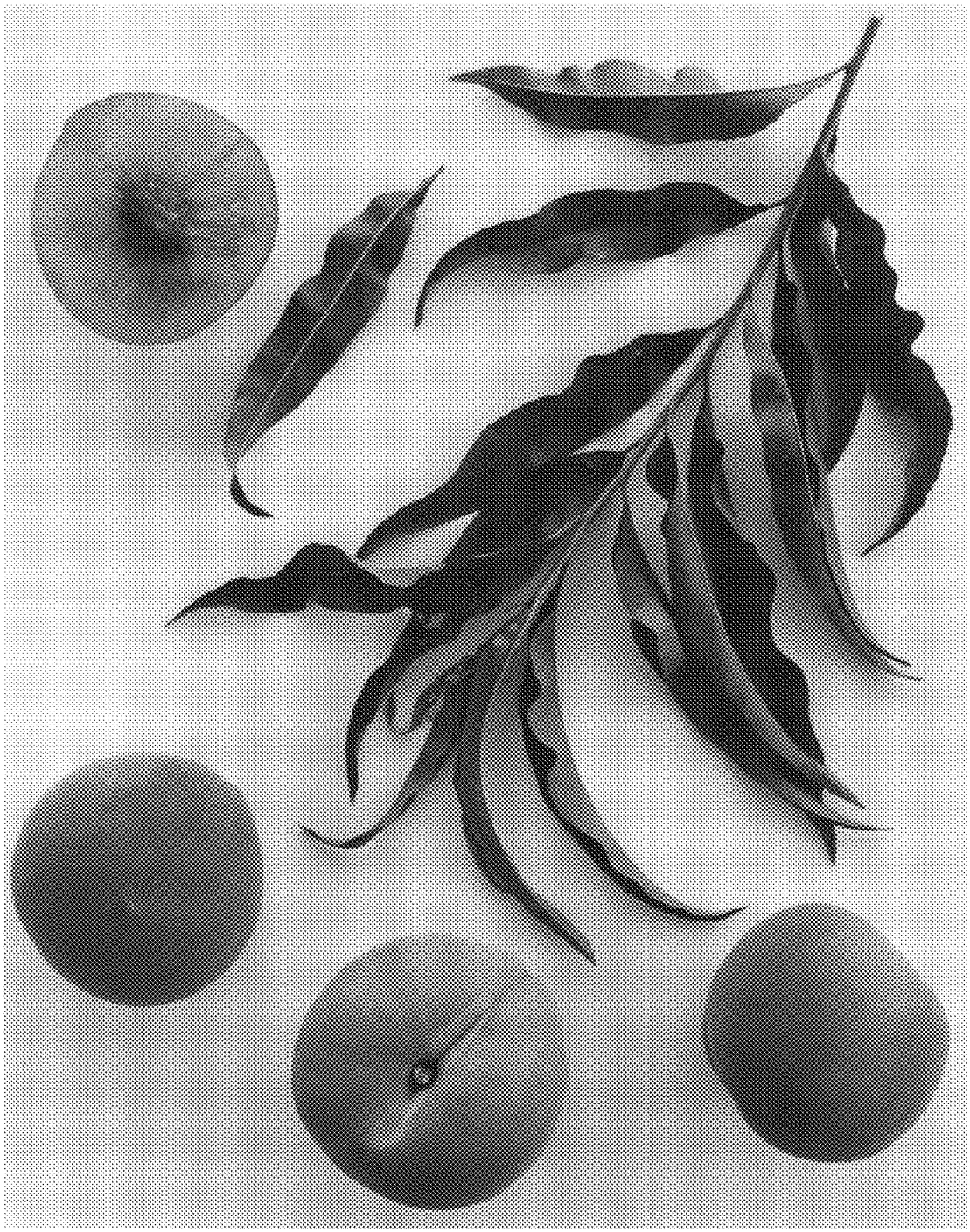

UNITED STATES PATENT AND TRADEMARK OFFICE

CERTIFICATE OF CORRECTION

PATENT NO. : PP 12,507 P2
DATED : April 2, 2002
INVENTOR(S) : John K. Slaughter et al.

It is certified that error appears in the above-identified patent and that said Letters Patent is hereby corrected as shown below:

Column 3,
Line 3, replace “commom” with -- common --.

Column 7,
Line 2, replace “Gererally” with -- Generally --.
Line 15, replace “freguently” with -- frequently --.
Line 35, replace “wings.” with -- wings --.

Column 8,
Line 38, replace “havesting” with -- harvesting --.

Signed and Sealed this

Fourteenth Day of January, 2003

JAMES E. ROGAN
*Director of the United States Patent and Trademark Office*